(12) United States Patent
Levy et al.

(10) Patent No.: US 9,126,215 B1
(45) Date of Patent: Sep. 8, 2015

(54) FLUID DISPERSION ASSEMBLY

(71) Applicants: Marc Levy, Miami, FL (US); Craig Huck, Waterford, PA (US); Steven Semoff, New City, NY (US)

(72) Inventors: Marc Levy, Miami, FL (US); Craig Huck, Waterford, PA (US); Steven Semoff, New City, NY (US)

(73) Assignee: Air Esscentials Inc., Miami, FL (US)

( * ) Notice: Subject to any disclaimer, the term of this patent is extended or adjusted under 35 U.S.C. 154(b) by 285 days.

(21) Appl. No.: 13/838,364

(22) Filed: Mar. 15, 2013

Related U.S. Application Data (60) Provisional application No. 61/694,500, filed on Aug. 29, 2012.

(51) Int. Cl.
  *B05B 7/06* (2006.01)
  *B05B 15/00* (2006.01)

(52) U.S. Cl.
  CPC ...................................... *B05B 15/00* (2013.01)

(58) Field of Classification Search
  CPC ...... B05B 7/005; B05B 7/0425; B05B 7/2405
  USPC .......................... 239/427, 337, 338, 426, 433
  See application file for complete search history.

(56) References Cited

U.S. PATENT DOCUMENTS

| | | | |
|---|---|---|---|
| 7,878,418 B2 | 2/2011 | Sevy | |
| 7,913,933 B2 | 3/2011 | Van Roemburg | |
| 7,930,068 B2 | 4/2011 | Robert et al. | |
| D645,947 S | 9/2011 | Sevy | |
| 2009/0025794 A1* | 1/2009 | Dorendorf et al. | 137/1 |
| 2009/0317504 A1* | 12/2009 | Rajala et al. | 425/7 |

\* cited by examiner

*Primary Examiner* — Davis Hwu
(74) *Attorney, Agent, or Firm* — Malloy & Malloy, P.L.

(57) ABSTRACT

A fluid dispersion assembly comprises a diffusion unit disposed in fluid communication with a fluid container, the assembly being powered by a compressed air source. The diffusion unit at least partially defines a diffusion chamber, and includes a diffusion assembly containing an atomizer assembly which, in combination with the diffusion chamber, generates a fluid dispersion from a mixture of compressed air and an operative fluid, for example, fragrant oils, essential oils, odor neutralizers, disinfectants such as triethylene glycol, air sanitizers, etc. The diffusion unit may include a suppressor assembly and/or a silencer assembly to reduce the amount of noise generated during operation. In one alternate embodiment, a modified diffusion chamber is provided which functions as a suppression chamber, thereby reducing the noise generated during operation of the assembly.

9 Claims, 5 Drawing Sheets

FLUID DISPERSION ASSEMBLY

BACKGROUND OF THE INVENTION

1. Field of the Invention

This invention relates generally to the field of dispersion of various fluids including, but not limited to, fragrant oils, essential oils, odor neutralizers, disinfectants, e.g., triethylene glycol, air sanitizers, and the like, into a generally enclosed airspace.

2. Description of the Related Art

There are various devices that can be used to deliver fragrant oils, essential oils, as well as other fluids into the air. Spray cans are commonly used, however, such devices require a user to repeatedly and manually spray when and where necessary. Plug-in devices that heat oils for dispersion into the air are also commonly used, but they require constant heating of the oil via an electrical outlet, which consumes energy and poses a potential fire hazard.

Fluid diffusion devices utilizing forced and/or compressed air for delivery of fragrant oils, essential oils, or other liquids are desirable alternatives to spray cans and plug-in devices since they do not require heating or constant user interaction, however, they have drawbacks as well. One drawback of many known fluid diffusion devices utilizing forced air is that they tend to make an undesirable and often, depending on the location, such as an office of other place of business, a disruptive amount of noise when in operation. In particular, the release of a fluid dispersed in the forced and/or compressed air from such a device is often unacceptably noisy.

As such, there is a need for a fluid dispersion assembly that is designed to significantly reduce the amount of noise generated during operation. A further need exists for such a fluid dispersion assembly to not only operate more quietly, but to operate quietly while generating a fluid dispersion in air having a uniform particle size distribution, such that dosing of an airspace with a particular liquid, whether it be oil, sanitizer, disinfectant, etc., can be predicted within acceptable limits.

SUMMARY OF THE INVENTION

The present invention addresses the need for a forced air diffusion and dispersion assembly for fluids such as fragrant oils, essential oils, odor neutralizers, disinfectants, air sanitizers, etc., that significantly reduces the amount of noise generated during operation. In at least one embodiment, the present invention is directed to a fluid dispersion assembly which operatively engages a fluid container, and is powered by a compressed air source. The fluid dispersion assembly includes a diffusion unit having oppositely disposed ends, which at least partially defines a diffusion chamber. The diffusion chamber is structured so as to facilitate formation of a fluid dispersion comprising a plurality of substantially uniform droplets prior to discharge from the diffusion chamber.

In at least one embodiment, a cap is cooperatively configured in sealing engagement with one of the oppositely disposed ends of the diffusion unit. Furthermore, the cap may be removably attached to the diffusion unit. The cap includes a discharge port disposed in communication with the diffusion chamber such that the fluid dispersion can exit the diffusion chamber and into an airspace surrounding the fluid dispersion assembly, while the assembly is in use. In some embodiments, the cap may include a service access port disposed therethrough. The service access port may also include a service access plug removably disposed therein, wherein removal of the service access plug allows for removal, repair, and/or cleaning of the internal components of the fluid dispersion assembly.

The present fluid dispersion assembly, in at least one embodiment, further includes a container interconnect affixed to a different one of the oppositely disposed ends of the diffusion unit which is cooperatively structured to interconnect the diffusion unit to the fluid container in a substantially sealed relationship. In at least one embodiment, a sealing washer is provided to facilitate formation of the substantially sealed relationship, and a drip tube is disposed in an interconnecting relation between the diffusion chamber and the fluid container, in at least one further embodiment, to protect the sealing washer from contact with the operative fluid(s).

In one embodiment, a diffusion assembly is disposed in an operative engagement with the diffusion unit via a cartridge port. The diffusion assembly is removably engaged with the cartridge port, in at least one embodiment. In some embodiments, the cartridge port is disposed directly through the diffusion unit between the oppositely disposed ends. The cartridge port may be oriented on the diffusion unit such that the diffusion assembly is at a substantially perpendicular orientation to the diffusion unit upon engagement therewith. In at least one other embodiment, a cartridge port is disposed through the cap. The diffusion assembly comprises an atomizer assembly, which in one embodiment comprises an inlet channel, a mixing chamber, and an atomizer exhaust channel, wherein the inlet channel is interconnected to the compressed air source and the mixing chamber comprises a fluid inlet disposed in fluid communication with the fluid in the fluid container. Compressed air and fluid are initially mixed together in the mixing chamber to form a fluid dispersion.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
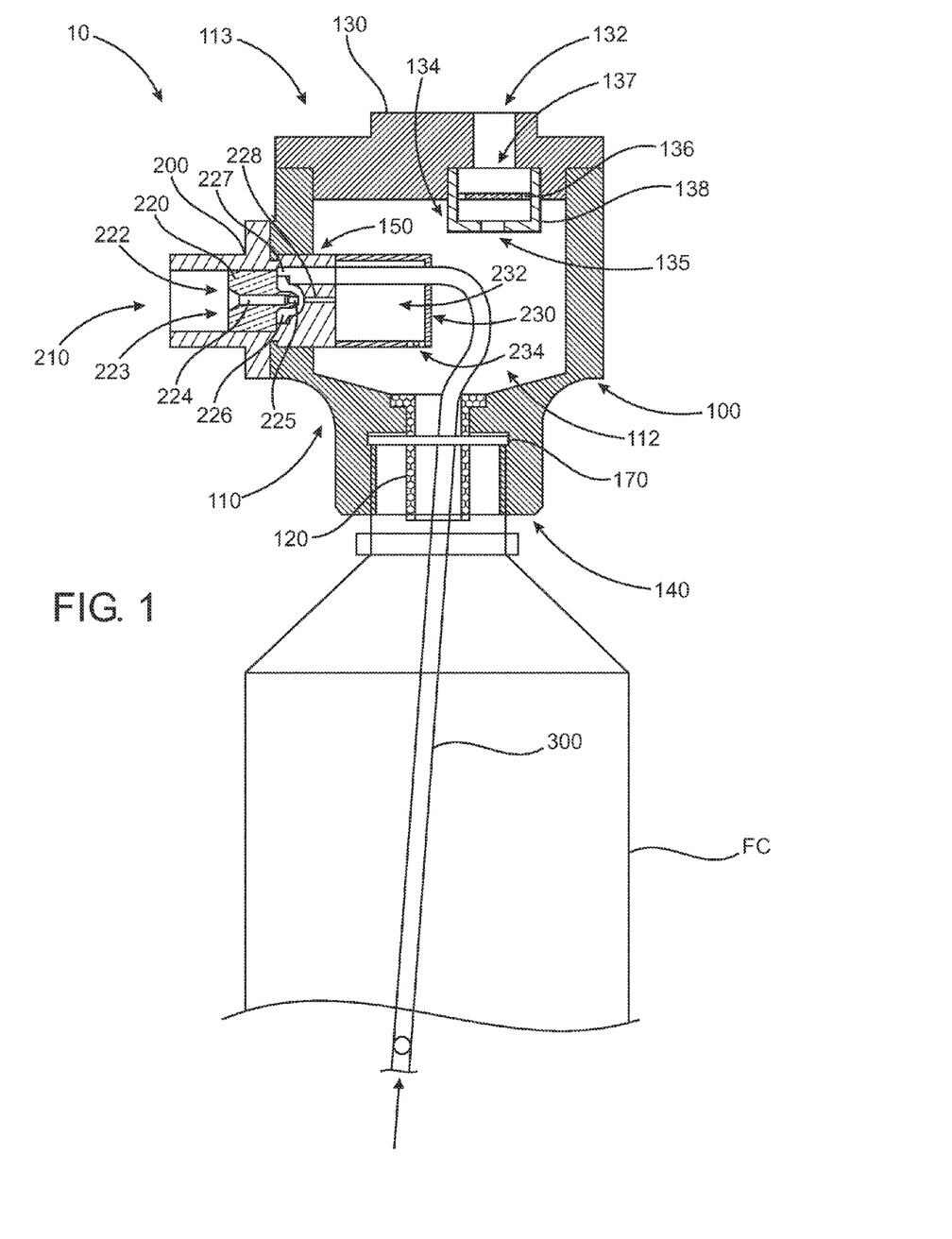
FIG. 1 is a cross-sectional elevation illustrative of one embodiment of a fluid dispersion assembly as disclosed in the present specification.
Figure 2:
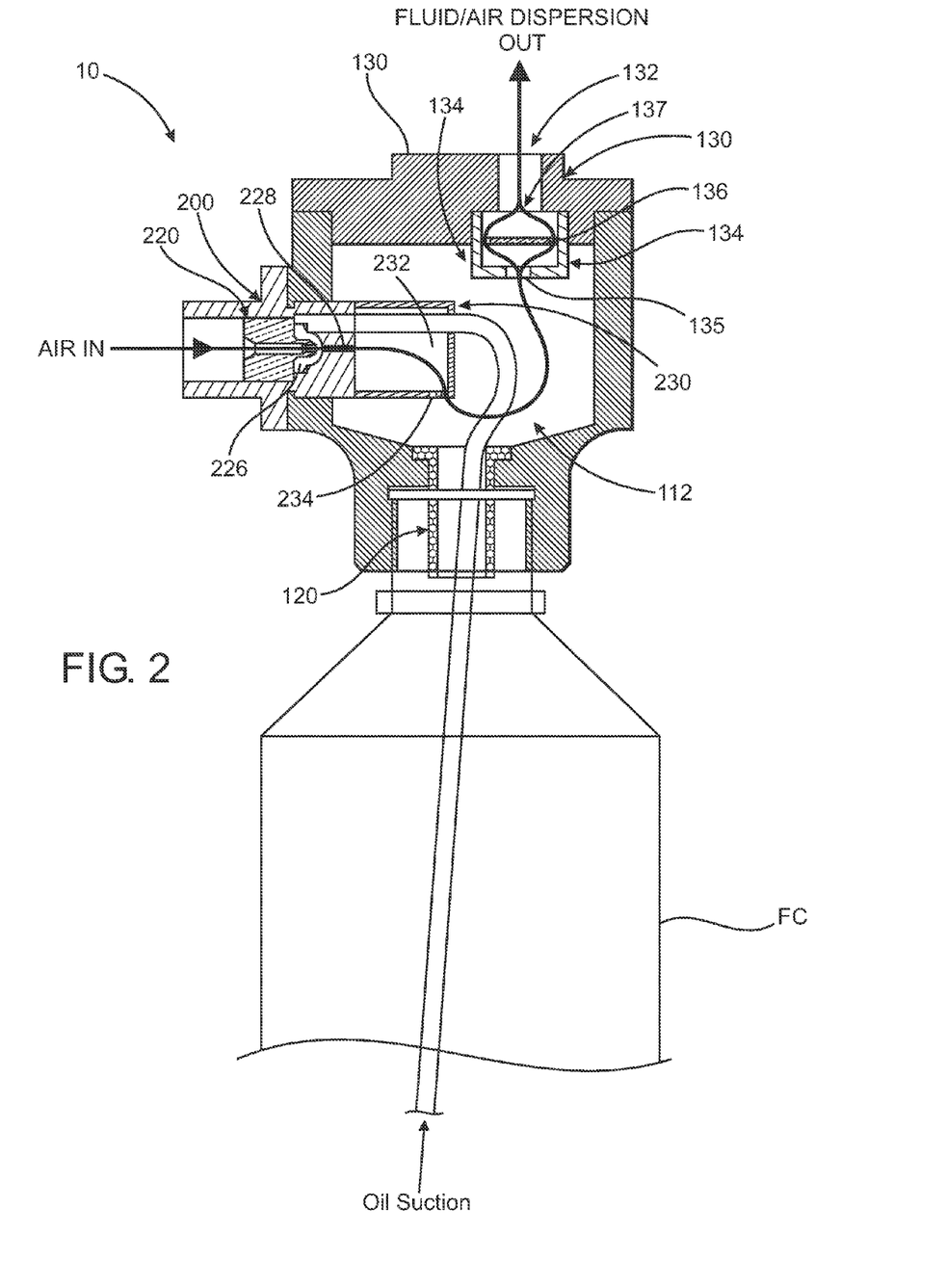
FIG. 2 is a cross-sectional elevation illustrative of another embodiment of a fluid dispersion assembly as disclosed in the present specification.

As illustrated in the accompanying figures, and with initial reference to FIGS. 1 and 2, the present invention is directed to a fluid dispersion assembly, generally indicated as 10, powered by a compressed air source. In at least one embodiment, the fluid dispersion assembly 10 is further structured to operatively engage a fluid container (FC). The fluid dispersion assembly 10 is structured to combine an amount of an operative fluid with compressed air to generate a fluid dispersion.

More in particular, a "fluid dispersion" in accordance with the present specification shall mean a mixture of an operative fluid in air comprising a plurality of substantially uniform droplets of the operative fluid dispersed throughout the air. Further, and once again, as used in the present specification, "substantially uniform droplets" shall mean droplets having substantially the same diameter. In at least one embodiment, the plurality of "substantially uniform droplets" each have a diameter in the range of about one micron (1 µm), in another embodiment, the diameter of the droplets is in the range of about three microns (3 µm), and, in one further embodiment, droplet diameter is in the range of about five microns (5 µm).

Figure 3:
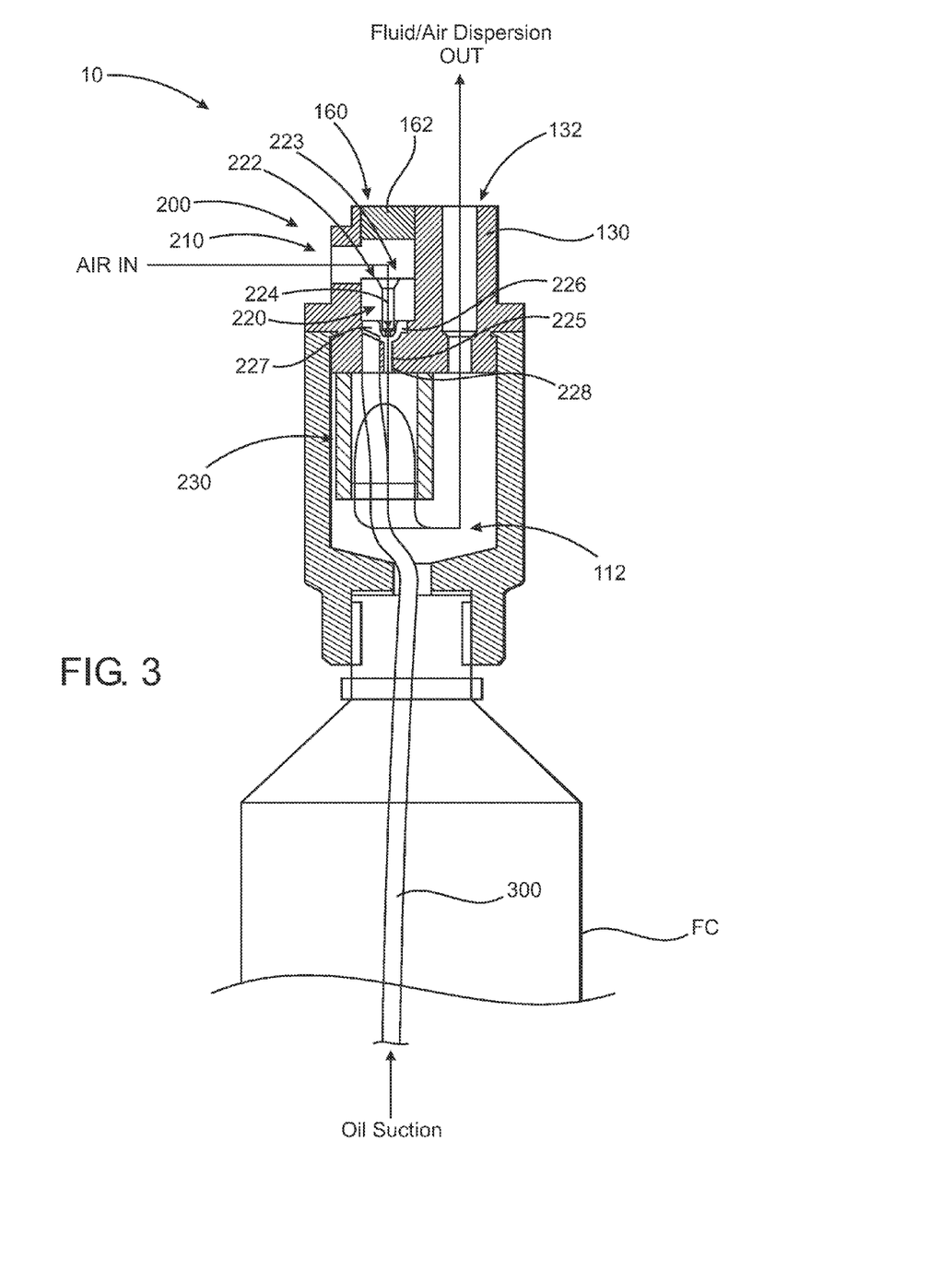
FIG. 3 is a cross-sectional view illustrative of yet another embodiment of a fluid dispersion assembly as disclosed in the present specification.
Figure 4:
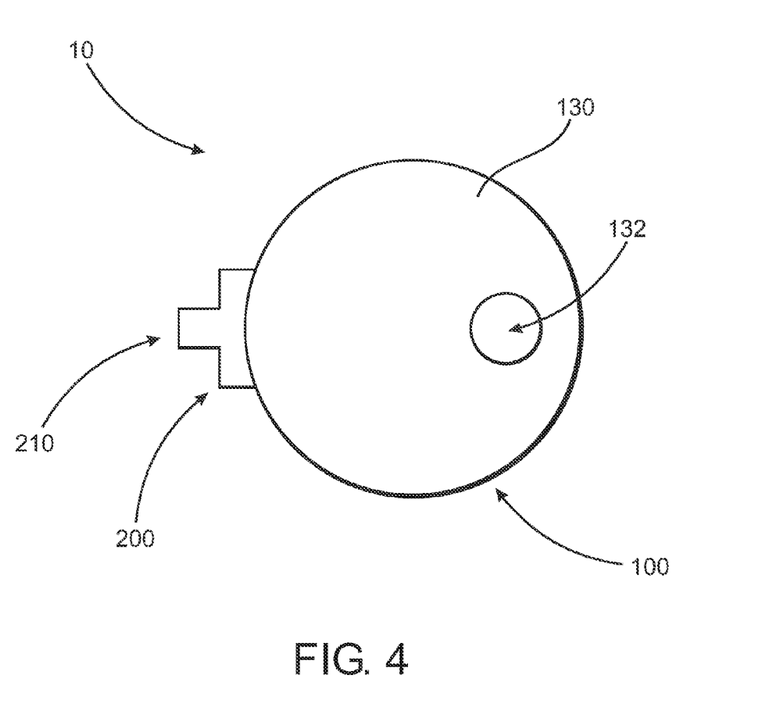
FIG. 4 is a plan view illustrative of an embodiment of a fluid dispersion assembly as disclosed in the present invention.

The fluid dispersion assembly 10 includes a diffusion unit 100 having oppositely disposed ends, as at 110 and 113, in at least one embodiment. The diffusion unit 100 at least partially defines a diffusion chamber 112, and in at least one embodiment, the diffusion chamber 112 is substantially enclosed within diffusion unit 100. The diffusion unit 100 may be constructed of any rigid material or materials which are chemically inert, or at least chemically resistant to the intended operative fluid(s) which include, but once again are not limited to, fragrant oils, essential oils, essential oil extracts, odor neutralizers, disinfectants, e.g., triethylene glycol, air sanitizers, etc. Further, the material of construction selected for the diffusion unit 100 must be capable of withstanding compressed air at operative pressures, which may range anywhere from about 5 to 50 psig, in most embodiments of the present fluid dispersion assembly 10. In one lower pressure embodiment, the operating pressure of the present fluid dispersion assembly 10 is in the range of about 5 to 10 psig, and in one further embodiment, the operating pressure is in a range of between about 5 to 7 psig. Conversely, a higher pressure embodiment of the present fluid dispersion assembly 10 operates at pressures in the range of about 20 to 25 psig, and in the range of between about 23 to 24 psig in yet one further embodiment. As such, the material or materials of construction of a diffusion unit 100 in accordance with the present specification may include metals, engineered plastic materials, e.g., polyvinyl chloride, high-density polyethylene, etc., and/or composite materials, just to name a few.

In one embodiment, a cap 130 is cooperatively configured and disposed in a sealing engagement with one of the oppositely disposed ends 110, 113 of the diffusion unit 100. The cap 130 includes a discharge port 132 therethrough in communication with the diffusion chamber 112, and provides a point of release of the fluid dispersion from the diffusion chamber 112 into the airspace surrounding the fluid dispersion assembly 10. In at least one embodiment, the cap 130 is removably attached in a sealing engagement to the diffusion unit 100. FIG. 4 is a plan view of the embodiment of the fluid dispersion assembly 10 as shown in FIGS. 1 and 2, and shows the cap 130 having a discharge port 132 disposed therethrough. As shown in the embodiment of FIG. 3, the cap 130 may include a service access port 160 disposed therethrough. The service access port 160 includes a service access plug 162 removably disposed therein, wherein removal of the service access plug 162 allows access for removal and cleaning or repair of a diffusion assembly 200, as disclosed in greater detail below.

The fluid dispersion assembly 10, in at least one embodiment, includes a container interconnect 140 which is cooperatively structured to interconnect the diffusion unit 100 to the fluid container (FC) in a substantially sealed relationship. In one embodiment, the container interconnect 140 is disposed at a different one of the oppositely disposed ends 110, 113, opposite of cap 130 of the diffusion unit 100. A sealing washer 170 is disposed between the diffusion unit 100 and the fluid container (FC), in at least one embodiment, so as to provide a substantially sealed relationship between the diffusion unit 100 and the fluid container (FC). The sealing washer 170 may be constructed from any of a variety of materials such as, but not limited to, rubber, nylon, plastic, PVC, TEFLON, or a composite material, once again, provided the material of construction is chemically inert or at least chemically resistant to the operative fluid(s).

In one further embodiment of a fluid dispersion assembly 10 in accordance with the present specification, a drip tube 120 is disposed in an interconnecting relation between the diffusion unit 100 and the fluid container (FC). As shown in the FIGS. 1 and 2, the drip tube 120 is disposed through a sealing washer 170, and thus, the drip tube 120 serves to minimize contact between the sealing washer 170 and the operative fluid, by essentially preventing the operative fluid from making contact in and around the sealing washer 170 disposed between the fluid container (FC) and the container interconnect 140. More in particular, the drip tube 120 channels any operative fluid which may agglomerate and/or accumulate in the diffusion chamber 112 through the drip tube 120 directly back into the fluid container (FC) without contacting the sealing washer 170, once again, as shown in FIGS. 1 and 2.

The container interconnect 140 may be structured in a variety of ways to allow interconnection to the fluid container (FC). As one example, the container interconnect 140 may be threaded, internally or externally, such that the diffusion unit 100 is interconnected to the fluid container (FC) by screwing the container interconnect 140 into place onto corresponding threads on the neck of the fluid container (FC). In at least one other embodiment, the container interconnect 140 comprises one portion of a quick-connect type fitting and the fluid container (FC) comprises a complimentary portion of such a quick-connect type fitting whereby once operatively engaged, a substantially sealed relationship is created between the diffusion unit 100 and the fluid container (FC). In at least some embodiments, the substantially sealed relationship is further enhanced by a sealing washer 170, as disclosed above.

In at least one embodiment, a cartridge port 150 is provided into the diffusion chamber 112 to facilitate operative engagement of a diffusion assembly 200 with the diffusion chamber 112. The diffusion assembly 200 may be removably engaged with the cartridge port 150 to aid in removal and replacement and/or cleaning of the diffusion assembly 200 and/or components thereof. In some embodiments, the cartridge port 150 is disposed directly through the diffusion unit 100 and into the diffusion chamber 112, and is positioned between the oppositely disposed ends 110, 113. In at least one embodiment, the cartridge port 150 is disposed on the diffusion unit 100 such that the diffusion assembly 200 is disposed in a substantially perpendicular orientation relative to the diffusion unit 100 when operatively engaging the cartridge port 150, such as is shown in the illustrative embodiment of FIG. 1. The diffusion assembly 200 is also shown disposed substantially perpendicular to the diffusion unit 100 in the plan view of FIG. 4. In at least one other embodiment, the cartridge port 150 is disposed through the cap 130. In yet another embodiment, the diffusion assembly 200 comprises an integral component of the cap 130 itself, such as in the embodiment of FIG. 3.

As illustrated in FIGS. 1 and 3, the diffusion assembly 200 comprises an air inlet 210 and an atomizer assembly 220. The atomizer assembly 220 comprises an atomizer air inlet channel 222, a mixing chamber 226, and an atomizer exhaust channel 228. The atomizer air inlet channel 222 is interconnected to the compressed air source via the air inlet 210. Moreover, the atomizer air inlet channel 222 may also include an inlet aperture 223, a first portion 224 and a second portion 225. The first portion 224 and the second portion 225 are collectively structured to facilitate delivery of compressed air into the mixing chamber 226. The first portion 224 of the atomizer air inlet channel 222 may comprise a larger diameter than the second portion 225, such as is shown in the illustrative embodiment of FIG. 1. Of course, it is within the scope and intent of the present invention for the atomizer air inlet channel 222 to comprise a constant diameter along its entire length, i.e., a diameter of a first portion is substantially equal to a diameter of a second portion.

Further, the mixing chamber 226 comprises a fluid inlet 227 disposed in fluid communication with an operative fluid in the fluid container (FC) via a fluid delivery tube 300. The fluid delivery tube 300 is disposed in a fluid communicating relation between the atomizer assembly 220 and the fluid container (FC) to facilitate delivery of an amount of the operative fluid into the atomizer assembly 220. In at least one embodiment, the fluid delivery tube 300 connects to the atomizer assembly 220 via the fluid inlet 227 into the mixing chamber 226.

As shown in FIGS. 1 and 2, the fluid inlet 227 is substantially perpendicular to a compressed air flowpath through the atomizer assembly 200. More in particular, and with reference to FIG. 1, the compressed air flowpath extends horizontally through the air inlet 210, atomizer air inlet channel 222, mixing chamber 226, and out through the atomizer exhaust 228.

Figure 5:
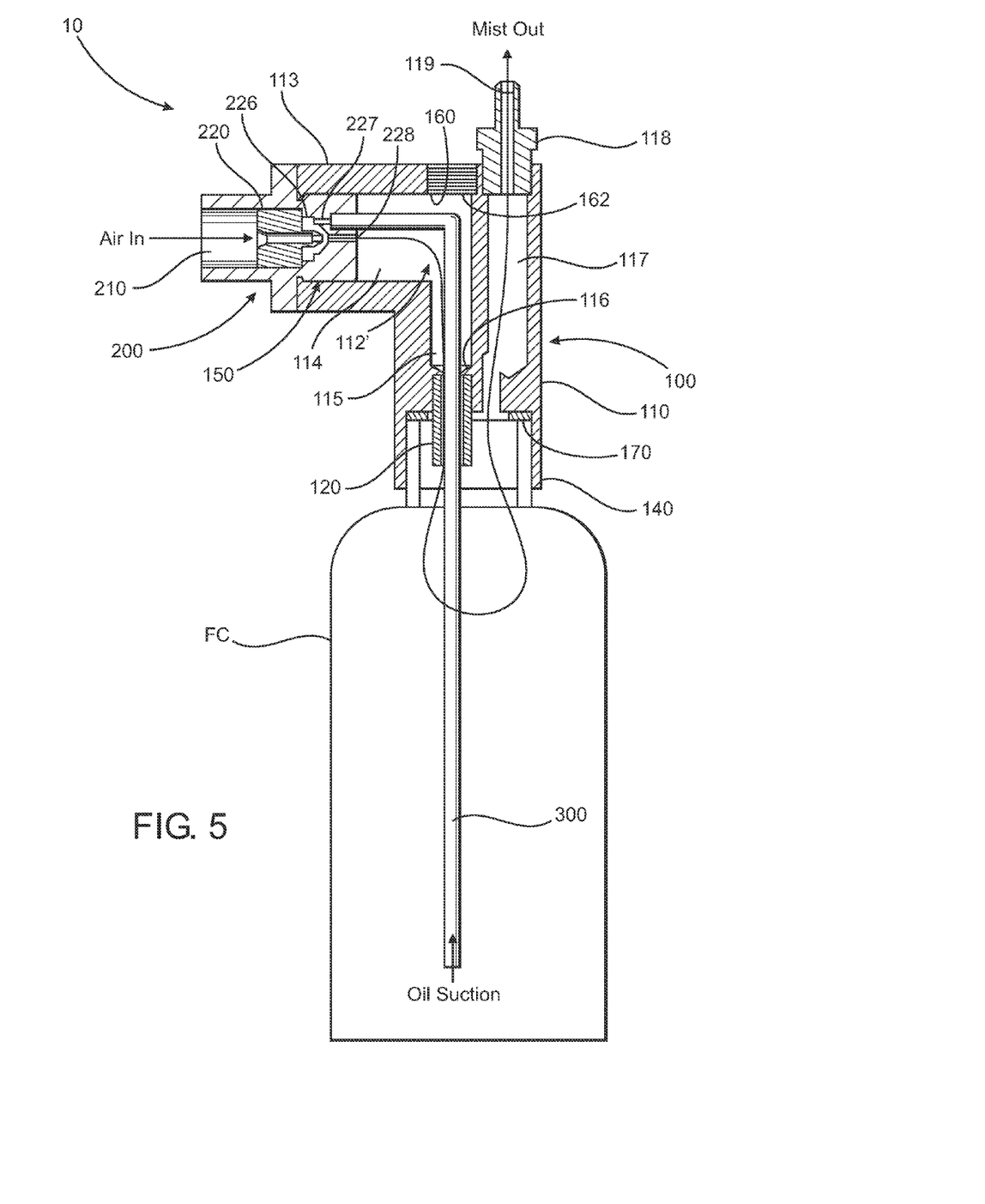
FIG. 5 is a cross-sectional elevation illustrative of one further embodiment of a fluid dispersion assembly in accordance with the present specification.

As such, when compressed air is supplied to the diffusion assembly 200, a corresponding amount of operative fluid is drawn into the mixing chamber 226 through the fluid delivery tube 300 as a result of the venturi effect of the compressed air flowing past the opening of the fluid inlet 227 into the mixing chamber 226. More in particular, at each different compressed air flowrate, i.e., each "predetermined amount" of compressed air which is dictated and fixed by a compressed air operating pressure supplied to diffusion assembly 200, a different corresponding and substantially constant amount, i.e., a "preselected amount" of an operative fluid corresponding to each different predetermined amount of compressed air, will be drawn into the mixing chamber 226. More importantly, the "predetermined amount" of compressed air and the "preselected amount" of the operable fluid are initially mixed together in the mixing chamber 226 to form a fluid dispersion. The diffusion chamber 112 is further structured to facilitate the formation of a plurality of substantially uniform droplets, as defined herein, in the fluid dispersion prior to discharge from the diffusion chamber 112 through discharge port 132.

As illustrated in FIGS. 1 and 3, the fluid dispersion assembly 10 also includes a suppressor assembly 230 disposed in communication with the diffusion assembly 200. The suppressor assembly 230 comprises a suppression chamber 232, disposed in a communicating relation with the atomizer exhaust channel 228 of the atomizer assembly 220. More in particular, the suppression chamber 232 receives the fluid dispersion from the mixing chamber 226. The suppressor assembly 230 helps to suppress the noise generated during operation of the fluid dispersion assembly 10 as it disrupts the path of flow of the fluid dispersion out of the atomizer assembly 200 and into diffusion chamber 112, and therefore, disrupts and dampens the sound waves associated therewith. Further, the walls of the suppressor assembly 230 itself serve to absorb and dampen the sound waves generated by the flow of the fluid dispersion out of the mixing chamber 236 through atomizer exhaust channel 238.

The suppressor assembly 230 may also include a suppressor discharge port 234 to facilitate transfer of the fluid dispersion from the suppressor chamber 232 into the diffusion chamber 112. In at least one embodiment, such as is shown in FIG. 1, the suppressor discharge port 234 is located through a low point in the suppressor chamber 232. Of course, as shown in the alternative embodiment of FIG. 2, the suppressor discharge port 234 is located through the sides of the suppressor chamber 232.

FIG. 5 is illustrative of an alternative embodiment of a fluid dispersion assembly 10, wherein a modified diffusion chamber 112' is configured to suppress and/or dampen sound waves generated during operation, similar to the suppressor assembly 230 disclosed above. However, as will be appreciated from the following disclosure, the diffusion chamber 112' of the embodiment of FIG. 5 serves to suppress sound waves generated during operation without the need for a separate suppression chamber, as in previously disclosed embodiments.

Before addressing the modified diffusion chamber 112' of the embodiment of FIG. 5, it is noted that, in many respects, the fluid dispersion assembly 10 of FIG. 5 is similar to the previously disclosed embodiments herein. To begin, the fluid dispersion assembly 10 of FIG. 5 comprises a diffusion unit 100 having oppositely disposed ends 110, 113, and a diffusion chamber 112' disposed therebetween. Unlike previously disclosed embodiments, however, the fluid dispersion assembly 10 of FIG. 5 includes a service access port 160 having a removable service access plug 162 disposed directly through one end 113 of the diffusion unit 100, rather than through a separate cap disposed at one end of the unit 100.

The fluid dispersion assembly 10 of FIG. 5 further comprises a container interconnect 140 cooperatively structured to interconnect the diffusion unit 100 to a fluid container (FC) in a substantially sealed relationship and, as before, a sealing washer 170 is provided to maintain a substantially sealed relationship.

A cartridge port 150 is disposed through one side of the diffusion unit 100, in the illustrative embodiment of FIG. 5, and a diffusion assembly 200 is operatively positioned therethrough and into fluid communication with diffusion chamber 112', as in previously disclosed embodiments. The diffusion cartridge 200 includes an air inlet 210 disposed in communication with an atomizer assembly 220. Further, and as in previously disclosed embodiments, when compressed air is supplied to the diffusion assembly 200, and more in particular, atomizer assembly 220, through air inlet 210, a corresponding amount of fluid is drawn into a mixing chamber 226 from the fluid container (FC) through a fluid delivery tube 300, as a result of the venturi effect of compressed air flowing past the opening of a fluid inlet 227 into the mixing chamber 226. As a result, a fluid dispersion is formed and discharged from the atomizer assembly 220 through atomizer exhaust channel 228, and directly into diffusion chamber 112'.

As noted above, and as may be seen with reference to FIG. 5, the diffusion chamber 112' of the present embodiment comprises a modified configuration. Specifically, the modified diffusion chamber 112' comprises an upside down L-shaped configuration, wherein a first axial portion 114 of the diffusion chamber 112' is disposed in a substantially axial orientation adjacent and relative to the discharge of the atomizer exhaust channel 228. A second transverse portion 115 of the diffusion chamber 112' is disposed in a substantially downwardly directed orientation, as shown in FIG. 5, substantially transverse or perpendicular to the direction of flow from atomizer exhaust channel 228.

The second or transverse portion 115 of the modified diffusion chamber 112', in at least one embodiment, comprises a fluid return lip 116 disposed at a lower end thereof in a surrounding relation to incoming fluid delivery tube 300. The fluid return lip 116, in at least one embodiment, extends downwardly and outwardly from the walls of the second portion 115 of the diffusion chamber 112', such that any liquid which coalesces in the diffusion chamber 112' along the walls thereof, will be directed into drip tube 120, disposed in an abutting relation along the underside of the fluid return lip 116, and back into fluid container (FC).

More importantly, the fluid dispersion discharged from the atomizer assembly 220 through atomizer exhaust channel 228 into diffusion chamber 112' is interrupted and redirected by virtue of axial portion 114 and transverse portion 115 therein. The interruption and redirection of flow in the modified diffusion chamber 112' during operation of the fluid dispersion assembly 10 in accordance with the present embodiment, serves to suppress or dampen sound waves generated therein, in a similar manner as the suppression chamber 232 of previously disclosed embodiments. Further, the restricted discharge from the transverse portion 115 of the modified diffusion chamber 112' may serve to further suppress or dampen sound waves, thus reducing the noise generated during operation to an even greater extent.

After being discharged from the diffusion chamber 112', the fluid dispersion enters the freeboard above the liquid in the fluid container (FC), the freeboard serving as a quasi-diffusion chamber prior to final discharge of the fluid dispersion from the diffusion unit 100. A discharge chamber 117 is disposed in fluid communication with the freeboard of the fluid container (FC), such that the fluid dispersion can pass therethrough, into a discharge head 118 and out through discharge channel 119 into the airspace surrounding the fluid dispersion assembly 10, as shown in the illustrative embodiment of FIG. 5.

In at least one embodiment, a fluid dispersion assembly 10 in accordance with the present specification further includes a silencer assembly 134 in communication with the discharge port 132, such as is illustrated in FIGS. 1 and 2. The silencer assembly 134 serves to further minimize the amount of noise generated during operation of the fluid dispersion assembly 10. The silencer assembly 134 comprises a baffle 136 disposed in a silencer chamber 138 between a silencer inlet 135 and a silencer outlet 137. The baffle 136 is structured and disposed to further disrupt the flow of the fluid dispersion through the fluid dispersion assembly 10, and more specifically, through the silencer chamber 138. In at least one embodiment, the silencer inlet 135 is disposed relative to the baffle 136 to at least partially, if not substantially, direct the flow of the fluid dispersion towards the baffle 136, so as to maximize the disruption of flow. Once again, as disclosed above with regard to the suppressor assembly 230, the disruption in the flow of the fluid dispersion though the silencer assembly 134 also creates a disruption and dampening of the sound waves associated therewith. As a result, the amount of noise generated during the operation of a fluid dispersion assembly 10 in accordance with the present specification is significantly reduced.

It is further envisioned that at least one embodiment of the fluid dispersion assembly 10 of the present invention is operated via a programmable timer to control a fragrance intensity and character in an airspace by metering the fragrance delivered in an enclosed environment. The fluid dispersion assembly 10 delivers a specific amount of a fragrance, i.e., the delivery rate, based upon such factors as the specific physical configuration of the atomizer assembly 220 and the fluid container (FC)/fluid delivery tube 300, the pressure and volume of the compressed air supplied into air inlet 210, as well as the physical properties of the fragrance itself, such as, viscosity, surface tension, vapor pressure, etc., wherein the delivery rate is measured in grams per minute of a fragrance dispersed. The perceived fragrance intensity in a specific airspace is measured from a sensory point of view using a labeled magnitude scale. The data is directly correlated to the amount of fragrance delivered and may be measured in either grams per liter or grams per cubic meter. Since the delivery rate is fixed, fragrance intensity is controlled by cycling the fluid dispersion assembly 10 through an on/off programming cycle every minute to deliver the intensity and character levels that are desired by a user. The optimization process is a function of dosing time per minute and a user's desired fragrance experience.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A fluid dispersion assembly disposable into an operative engagement with a fluid container which contains an operative fluid and a compressed air source, said fluid dispersion assembly generating a fluid dispersion comprising a plurality of substantially uniform droplets of the operative fluid in air and discharging the fluid dispersion into an airspace surrounding said fluid dispersion assembly, said fluid dispersion assembly comprising:

a diffusion unit having oppositely disposed ends, wherein said diffusion unit at least partially defines a substantially enclosed diffusion chamber, a cap cooperatively configured and disposed in a sealing engagement with one of said oppositely disposed ends of said diffusion unit, a service access port through said cap at least partially defining an access opening, and a service access plug removably disposable in a substantially sealing engagement with said access opening of said service access port, a discharge port disposed in fluid communication between said diffusion chamber and the airspace surrounding said fluid dispersion assembly, a diffusion assembly disposed in an operative engagement with said diffusion unit via a cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the operative fluid in the fluid container, wherein the compressed air and the operative fluid are mixed together in said mixing chamber to form the fluid dispersion, a suppressor assembly disposed in communication with said diffusion assembly, said suppressor assembly comprising a suppression chamber structured to dampen sound waves generated during operation of said fluid dispersion assembly, and said diffusion chamber structured to facilitate formation of the plurality of substantially uniform fluid droplets of the fluid dispersion prior to discharge of the fluid dispersion from said diffusion chamber through said discharge port and into the airspace.

2. A fluid dispersion assembly disposable into an operative engagement with a fluid container which contains an operative fluid and a compressed air source, said fluid dispersion assembly generating a fluid dispersion comprising a plurality of substantially uniform droplets of the operative fluid in air and discharging the fluid dispersion into an airspace surrounding said fluid dispersion assembly, said fluid dispersion assembly comprising:

a diffusion unit having oppositely disposed ends, wherein said diffusion unit at least partially defines a substantially enclosed diffusion chamber, a cap cooperatively configured and disposed in a sealing engagement with one of said oppositely disposed ends of said diffusion unit, a discharge port disposed in fluid communication between said diffusion chamber and the airspace surrounding said fluid dispersion assembly, a diffusion assembly disposed in an operative engagement with said diffusion unit via a cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the operative fluid in the fluid container, wherein the compressed air and the operative fluid are mixed together in said mixing chamber to form the fluid dispersion, a suppressor assembly disposed in communication with said diffusion assembly, said suppressor assembly comprising a suppression chamber structured to dampen sound waves generated during operation of said fluid dispersion assembly, said atomizer exhaust channel is disposed in a communicating relation between said mixing chamber and said suppression chamber to facilitate transfer of the fluid dispersion therebetween, and said diffusion chamber structured to facilitate formation of the plurality of substantially uniform fluid droplets of the fluid dispersion prior to discharge of the fluid dispersion from said diffusion chamber through said discharge port and into the airspace.

3. The assembly of claim 2 wherein said suppressor assembly further comprises a suppressor discharge port disposed between said suppression chamber and said diffusion chamber to facilitate transfer of the fluid dispersion from said suppression chamber into said diffusion chamber.

4. A fluid dispersion assembly disposable into an operative engagement with a fluid container which contains an operative fluid and a compressed air source, said fluid dispersion assembly generating a fluid dispersion comprising a plurality of substantially uniform droplets of the operative fluid in air and discharging the fluid dispersion into an airspace surrounding said fluid dispersion assembly, said fluid dispersion assembly comprising:

a diffusion unit having oppositely disposed ends, wherein said diffusion unit at least partially defines a substantially enclosed diffusion chamber, a cap cooperatively configured and disposed in a sealing engagement with one of said oppositely disposed ends of said diffusion unit, a discharge port disposed in fluid communication between said diffusion chamber and the airspace surrounding said fluid dispersion assembly, a diffusion assembly disposed in an operative engagement with said diffusion unit via a cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the operative fluid in the fluid container, wherein the compressed air and the operative fluid are mixed together in said mixing chamber to form the fluid dispersion, a suppressor assembly disposed in communication with said diffusion assembly, said suppressor assembly comprising a suppression chamber structured to dampen sound waves generated during operation of said fluid dispersion assembly, said diffusion chamber structured to facilitate formation of the plurality of substantially uniform fluid droplets of the fluid dispersion prior to discharge of the fluid dispersion from said diffusion chamber through said discharge port and into the airspace, and a silencer assembly having a silencer inlet, a silencer outlet, and a baffle, wherein said baffle partially restricts movement of the fluid dispersion through said silencer chamber from said silencer inlet to said silencer outlet, thereby dampening sound waves generated during operation of said fluid dispersion assembly.

5. A fluid dispersion assembly disposable into an operative engagement with a fluid container which contains an operative fluid and a compressed air source, said fluid dispersion assembly generating a fluid dispersion comprising a plurality of substantially uniform droplets of the operative fluid in air and discharging the fluid dispersion into an airspace surrounding said fluid dispersion assembly, said fluid dispersion assembly comprising:

a diffusion unit having oppositely disposed ends, wherein said diffusion unit at least partially defines a substantially enclosed diffusion chamber, a cap cooperatively configured and disposed in a sealing engagement with one of said oppositely disposed ends of said diffusion unit, a discharge port disposed in fluid communication between said diffusion chamber and the airspace surrounding said fluid dispersion assembly, a diffusion assembly disposed in an operative engagement with said diffusion unit via a cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the operative fluid in the fluid container, wherein the compressed air and the operative fluid are mixed together in said mixing chamber to form the fluid dispersion, a suppressor assembly disposed in communication with said diffusion assembly, said suppressor assembly comprising a suppression chamber structured to dampen sound waves generated during operation of said fluid dispersion assembly, said diffusion chamber structured to facilitate formation of the plurality of substantially uniform fluid droplets of the fluid dispersion prior to discharge of the fluid dispersion from said diffusion chamber through said discharge port and into the airspace, a container interconnect mounted to a different one of said oppositely disposed ends of said diffusion unit and cooperatively structured to interconnect said diffusion unit to the fluid container in a substantially sealed relationship, wherein said container interconnect comprises a sealing washer disposed between said diffusion unit and the fluid container to maintain said substantially sealed relationship, and a drip tube, said drip tube disposed in an interconnecting relation between said diffusion chamber and the fluid container through said sealing washer, wherein said drip tube minimizes contact between said sealing washer and the operative fluid.

6. A fluid dispersion assembly operable with a preselected fluid in a fluid container and a compressed air source, said fluid dispersion assembly generating a fluid dispersion comprising a plurality of substantially uniform droplets of the preselected fluid in air and discharging the fluid dispersion into an airspace surrounding said fluid dispersion assembly, said fluid dispersion assembly comprising:

a diffusion unit defining a substantially enclosed diffusion chamber, said diffusion chamber comprising oppositely disposed portions therein, a cartridge port disposed through a portion of said diffusion unit and into said diffusion chamber, a diffusion assembly disposed in an operative engagement with said cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the preselected fluid in the fluid container, wherein the compressed air and the preselected fluid are mixed together in said mixing chamber to form the fluid dispersion, one of said oppositely disposed portions of said diffusion chamber comprises an axial portion disposed in an adjacent substantially axial orientation relative to said atomizer exhaust channel, another of said oppositely disposed portions of said diffusion chamber comprises a transverse portion disposed in a spaced apart substantially perpendicular orientation relative to said atomizer exhaust channel, said diffusion chamber structured to facilitate formation of the plurality of substantially uniform fluid droplets in the fluid dispersion prior to discharge of the fluid dispersion from said diffusion chamber, wherein the fluid dispersion discharged from said atomizer exhaust channel into said diffusion chamber is interrupted and redirected in said axial portion and said transverse portion, thereby dampening sound waves generated during operation of said fluid dispersion assembly, and a discharge chamber disposed in fluid communication with said diffusion chamber and a discharge head, said discharge head comprising a discharge channel disposed to direct the fluid dispersion from said discharge chamber into the airspace surrounding said fluid dispersion assembly.

7. A fluid dispersion assembly operable with a preselected fluid in a fluid container and a compressed air source, said fluid dispersion assembly generating a fluid dispersion comprising a plurality of substantially uniform droplets of the preselected fluid in air and discharging the fluid dispersion into an airspace surrounding said fluid dispersion assembly, said fluid dispersion assembly comprising:

a diffusion unit defining a substantially enclosed diffusion chamber, said diffusion chamber comprising oppositely disposed portions therein, a cartridge port disposed through a portion of said diffusion unit and into said diffusion chamber, a diffusion assembly disposed in an operative engagement with said cartridge port, wherein said diffusion assembly comprises an atomizer assembly, said atomizer assembly comprising an atomizer air inlet channel, a fluid inlet, a mixing chamber, and an atomizer exhaust channel, said atomizer air inlet channel interconnected to the compressed air source and said fluid inlet disposed in fluid communication with the preselected fluid in the fluid container, wherein the compressed air and the preselected fluid are mixed together in said mixing chamber to form the fluid dispersion, one of said oppositely disposed portions of said diffusion chamber comprises an axial portion disposed in an adjacent substantially axial orientation relative to said atomizer exhaust channel, another of said oppositely disposed portions of said diffusion chamber comprises a transverse portion disposed in a spaced apart substantially perpendicular orientation relative to said atomizer exhaust channel, wherein said transverse portion comprises a fluid return lip disposed at a lower end thereof and a drip tube disposed adjacent and abutting said fluid return lip, said diffusion chamber structured to facilitate formation of the plurality of substantially uniform fluid droplets in the fluid dispersion prior to discharge of the fluid dispersion from said diffusion chamber, and a discharge chamber disposed in fluid communication with said diffusion chamber and a discharge head, said discharge head comprising a discharge channel disposed to direct the fluid dispersion from said discharge chamber into the airspace surrounding said fluid dispersion assembly.

8. The assembly as recited in claim 7 wherein said fluid return lip is disposed to direct coalesced fluid from said diffusion chamber into said drip tube.

9. The assembly as recited in claim 8 wherein said drip tube is disposed to direct said coalesced fluid into the fluid container.

* * * * *